United States Patent
Di Girolamo et al.

(10) Patent No.: US 11,020,440 B2
(45) Date of Patent: Jun. 1, 2021

(54) PROBIOTIC FOR THE TREATMENT OF PSORIASIS

(71) Applicants: Stefano Di Girolamo, Rome (IT); Laura Diluvio, Rome (IT); Arianna Zangrilli, Rome (IT)

(72) Inventors: Stefano Di Girolamo, Rome (IT); Laura Diluvio, Rome (IT); Arianna Zangrilli, Rome (IT)

( * ) Notice: Subject to any disclaimer, the term of this patent is extended or adjusted under 35 U.S.C. 154(b) by 0 days.

(21) Appl. No.: 16/963,933

(22) PCT Filed: Jan. 24, 2019

(86) PCT No.: PCT/EP2019/051778
§ 371 (c)(1),
(2) Date: Jul. 22, 2020

(87) PCT Pub. No.: WO2019/145438
PCT Pub. Date: Aug. 1, 2019

(65) Prior Publication Data
US 2020/0405783 A1    Dec. 31, 2020

(30) Foreign Application Priority Data
Jan. 26, 2018  (IT) ................ 102018000002052

(51) Int. Cl.
| | | |
|---|---|---|
| *A61K 35/741* | (2015.01) | |
| *A61K 35/744* | (2015.01) | |
| *A23L 2/52* | (2006.01) | |
| *A61P 17/06* | (2006.01) | |
| *A23L 33/135* | (2016.01) | |
| *A61K 9/00* | (2006.01) | |

(52) U.S. Cl.
CPC .............. *A61K 35/744* (2013.01); *A23L 2/52* (2013.01); *A23L 33/135* (2016.08); *A61P 17/06* (2018.01); *A61K 9/0053* (2013.01)

(58) Field of Classification Search
CPC .................................................. A61K 35/741
See application file for complete search history.

(56) References Cited

U.S. PATENT DOCUMENTS 10,828,350 B1 * 11/2020 Bermudes .............. A61K 38/55
2013/0216577 A1    8/2013 Farmer et al.

FOREIGN PATENT DOCUMENTS

EP         3222282 A1     9/2017
WO      2018185557 A1   10/2018

OTHER PUBLICATIONS

Di Pierro F. et al., "Positive clinical outcomes derived from using Streptococcus salivarius K12 to prevent streptococcal pharyngotonsillitis in children: a pilot investigation", Drug, Healthcare and Patient Safety, vol. 8, Nov. 21, 2016, pp. 77-81.

(Continued)

*Primary Examiner* — Rosanne Kosson
(74) *Attorney, Agent, or Firm* — Silvia Salvadori, P.C.; Silvia Salvadori

(57) ABSTRACT

The use of orally administrable compositions comprising *Streptococcus salivarius* is described, for the prevention or the treatment of psoriasis in all its forms. In particular, the present invention relates to the use of compositions comprising *Streptococcus salivarius*, for the treatment of psoriasis in all its forms.

11 Claims, 2 Drawing Sheets

(56) References Cited

OTHER PUBLICATIONS

International Preliminary Report on Patentability of PCT/EP2019/051778 dated Jan. 10, 2020.
Lukic J. et al., "Probiotics or pro-healers: the role of beneficial bacteria in tissue repair: the role of probiotics in wound healing", Wound Repair and Regeneration, vol. 25, No. 6, Nov. 1, 2017, pp. 912-922.
Search Report and Written Opinion of PCT/EP2019/051778 dated May 9, 2019.
Thorleifsdottir R.H. et al, "Improvement of psoriasis after tonsillectomy is associated with a decrease in the frequency of circulating T cells that recognize Streptococcal determinants and homologous skin determinants", The Journal of Immunology, vol. 188, No. 10, Apr. 9, 2012, pp. 5160-5165.

* cited by examiner

T4
PASI: 14

T0
PASI: 28

T12
PASI: 0,8

T8
PASI: 2,4

PROBIOTIC FOR THE TREATMENT OF PSORIASIS

This application is a U.S. national stage of PCT/EP2019/051778 filed on 24 Jan. 2019, which claims priority to and the benefit of Italian Application No. 102018000002052 filed on 26 Jan. 2018 the contents of which are all incorporated herein by reference in their entireties.

FIELD OF THE INVENTION

The present invention relates to an orally administrable composition useful for the prevention or the treatment of psoriasis.

In particular, the present invention relates to compositions suitable for the preparation of drugs, food supplements or medical devices, which can be orally administered, useful in the prevention or the treatment of psoriasis, comprising as active ingredient/main component *Streptococcus salivarius*.

BACKGROUND OF THE INVENTION

Psoriasis is a chronic, relapsing disease of the skin, which may occur at the skin level with different clinical aspects.

The causes of psoriasis are not fully understood however, this disease is linked to alterations of the immune system.

Various types of psoriasis are identified and, in some patients, different forms of this pathology may be present simultaneously.

The various types of psoriasis differ on the basis of different elements such as: morphology of the lesions (plaques, pustules, etc.), the degree of inflammation, the presence in only one part of the body or in more parts, the extension and the path of the lesion, the speed of propagation, etc.

The most typical medical classification makes a distinction according to the morphology of the lesions; on this basis, the types of psoriasis are classified as:
  psoriasis vulgaris or plaque psoriasis,
  guttate or eruptive psoriasis,
  pustular psoriasis,
  erythrodermic psoriasis,
  inverse (or reversed) psoriasis, and
  arthropathic psoriasis (or psoriatic arthritis).

Psoriasis vulgaris or plaque psoriasis is the most common form of psoriasis (80% of the cases). It displays well defined plaques on the palm of the hand, sole of the foot, elbows, knees and intergluteal area, and only occasionally on genitals. The lesions on the skin are red or salmon-coloured at the base and have silvery scales at the top. The disease arises with the appearance of small papules, which then progressively converge into larger plaques.

The lesions have a size greater than 1 cm in diameter and the edges are sharp and well defined, with symmetrical distribution, and having a shape from round to oval and irregular edges. The plaques in remission become clearer, at the centre first and then to the edges; along the edges the plaque usually remains longer. They appear all over the body, even if prevalently on the extending surfaces of elbows and knees, the scalp, the sacral region and the nails.

In most cases (about 80 percent), psoriasis vulgaris has a limited extension and treatment is represented by applications of topical products. Excellent results can be obtained with phototherapy targeted for treating the individual lesions (example: excimer laser). In the extended forms of psoriasis vulgaris (when the involvement is equal to or greater than 10 percent of the body surface), treatments administered orally or by injection (systemic therapies) are used.

Guttate or eruptive psoriasis, more rare than the psoriasis vulgaris, is characterized by the involvement of the trunk and upper limbs. Lesions appear as small formations (from a few millimeters up to 1.5 centimetres) having the form of a drop, poorly desquamating.

Guttate psoriasis occurs in 10% of the population of patients and frequently appears at a very young age (infance and adolescence), particularly within the same family. The appearance of the first lesions is often preceded by upper respiratory tract infections by *Streptococcus*-hemolytic group A in a subject genetically susceptible to psoriasis or, less frequently, by *Herpes zoster*. Despite this correlation, the antigen responsible for the disease has not been identified to date.

The therapy takes advantage of the use of emollients, corticosteroids for local use and phototherapy with narrow-band UV-B phototherapy. Regardless of the treatments carried out, over 30 percent of the patients develop psoriasis vulgaris.

Pustular psoriasis is characterised by the occurrence of vesicle lesions, with a diameter of about 0.5 cm, which are present on existing erythematosus plaques. With the time, the pustules become darker and flake off. The skin is locally irritated, reddened and sensitive. The appearance of pustules affects more frequently the palm of the hand and the sole of the foot. In some cases, pustular psoriasis can progress in plaque psoriasis, localized or extended. The onset of pustular psoriasis is related to previous infections, protracted stress or contact with chemical agents. The 50% of the patients suffering from pustular psoriasis also have arthritis.

The form with palmo-plantar involvement can be treated with topical therapies mainly based on cortisones. In the most resistant cases, patients will have to resort to targeted phototherapy or to the administration of systemic drugs.

The generalized form of pustular psoriasis is particularly severe, requires hospitalization and need of systemic therapies.

Erythrodermic psoriasis is the most severe form of psoriasis, the inflammatory process affecting the skin may involve up to 100% of the body surface. The skin completely loses its barrier functions against the external environment and of body temperature control. If not treated, it is the only form of psoriasis, which may lead to the death of the patient, usually for sepsis. Factors associated with onset of erythrodermic psoriasis include the intake of corticosteroids and prolonged exposure to sunlight.

Hospitalization is frequently necessary and treatment is based on systemic therapies.

In the inverse (or reversed) psoriasis, the injuries occur with reversed location with respect to the most common forms, namely at the level of skin folds, such as the armpits, the navel and the folds of overweight belly, genitals and the buttocks. In this case, the symptoms, especially burning and redness, are sharpened by perspiration and friction generated by contact with clothing.

The treatment of inverse psoriasis is based on products for local use, such as low potency corticosteroids, some derivatives of vitamin D and local immunosuppressive (tacrolimus, pimecrolimus).

Depending on the affected area, psoriasis can be classified into:
  psoriasis of the mucosa: it involves the oral mucosa and the tongue and it is common in pustular and erythrodermic psoriasis, but also in psoriasis vulgaris;

psoriasis of the nails: about 50% of the patients suffering from psoriasis is also affected to nail, but only in 5% of cases it is the only manifestation of the disease; the hands are more affected than the feet and in general more fingers are involved, although it may be limited to one fingernail;

psoriasis of the head and of the scalp;

arthropathic psoriasis (or psoriatic arthritis): defined as a seronegative arthritis, it is an inflammatory pathology of the joints often associated to psoriatic skin lesions. It is classified among the seronegative spondylitis, since there is the negativity of the Rheumatoid Factor (RF) and the absence of the characteristic rheumatoid nodules. The percentage of patients suffering from arthropathic psoriasis ranges from 5% to 42% of the patients suffering from psoriasis. Many patients develop arthropathic psoriasis many years after the psoriasis vulgaris and the severity of the involvement is not related to the severity of articular cutaneous manifestations. In 70% of the patients, the articular symptoms develop several years after the cutaneous manifestations; in 10-15% of the cases arthritis precedes psoriasis (family history is useful in the diagnosis) and in 15% of the patients, the cutaneous manifestations arise simultaneously with the arthropathy, up to sometimes reduce joint mobility. The main symptoms include pain and stiffness, swelling of the joints. In such patients, the use of systemic immunosuppressive drugs is mandatory as first line therapy.

More generally, the therapies employed for the treatment of psoriasis depend on the extension of the psoriatic lesions. Topical medications are indicated for limited forms of the disease and comprise keratolytic agents, such as salicylic acid, vitamin D analogues, steroids, tazarotene, dithranol and combinations thereof. In the forms more extended, systemic treatments are used and ultraviolet light.

The conventional treatments comprise cyclosporin, methotrexate, retinoids, fumaric acid derivatives (the latter only in some European countries), phototherapy and PUVA therapy (psoralenes and UV-A).

More recently, new drugs have been introduced, the so-called biological drugs that is, drugs obtained in living cells using genetic engineering techniques. The biological drugs approved for the treatment of psoriasis act on molecules or cells involved in the inflammatory or in the immune reaction and comprise the drugs anti-TNF-α (e.g. infliximab, etanercept and adalimumab), the inhibitors of T cells (alefacept, not available in Italy), inhibitory agents of IL-12/23 (ustekinumab).

*Streptococcus salivarius* is a gram-positive anaerobic bacterial species of spherical shape, which colonizes the mucosa of the mouth and the upper respiratory tract of human beings since a few hours after birth. Thanks to this colonization, *Streptococcus salivarius* prevents other potentially pathogenic bacteria to colonize the mucosa of the mouth and the respiratory tract thus avoiding serious infections to the child.

*S. salivarius* strains were tested for their use as probiotic in the prevention of oral infections. Some strains of *S. salivarius* are found to produce BLIS (bacteriocin-like inhibitory substances), which are antimicrobial peptides. These peptides show interspecies inhibition by inhibiting and/or significantly reducing throat infections by *Streptococcus pyogenes* [*Streptococcus salivarius* as model oral probiotics, Future Microbiology 2009, 4, (7): 819-835].

In Drug Healthc. Patient Saf. 2014; 6 15-20, the use of *Streptococcus salivarius* BLIS K12 is described for the prevention of infections by *Streptococci* and in cases of infant paratonsillitis.

In European Journal of Clinical Microbiology & Infectious Diseases, December 2008, 27:1261, experimental data on the colonisation of the upper respiratory tract in children by means of the use of an oral paediatric formulation of *Streptococcus salivarius* BLIS K12 are reported. *Streptococcus salivarius* BLIS K12 is the only active ingredient of the medical device BACTOBLIS® marketed in Italy by OMEOPIACENZA.

In Probiotics & Antimicro. Prot. (2010) 2:135-144, *S. salivarius* BLIS K12 is demonstrated to colonise the oral cavity of human volunteers.

In J. Med Micro June 2013 62: 875-88 studies showed that *Streptococcus salviarius* BLIS M18 was able to colonise human subjects with the observation of a subsequent reduced acquisition of the upper respiratory tract pathogen *Streptococcus pyogenes*, compared to placebo control group.

Blis Technologies Ltd (New Zealand) market several products internationally containing *S. salivarius* BLIS K12 or *S. salivarius* BLIS M18. These products include the dietary supplements ThroatGuard™ DailyDefence™ and ToothGuard™.

In Int. J. Gen. Med. 2017 Jun. 19; 10:171-175, the use of *Streptococcus salivarius* 24SMBc in combination with *Streptococcus oralis* 89a, administered by nasal spray, to prevent episodes of recurrent acute otitis media in children is described. *Streptococcus salivarius* 24SMBc is one of the two active ingredients of the medical devices OROGERMINA™ and RINOGERMINA® (marketed in Italy by D.M.G. S.r.l.) together with *Streptococcus oralis* 89a.

EP 3222282 claims a probiotic composition comprising *Bifidobacterium animalis* subs. *lactis* (*B. lactis*), *Bifidobacterium longum* and *Lactobacillus rhamnosus* in the treatment and/or prevention of psoriasis outbreaks or psoriasis.

US 2013/0216577 claims a method of reducing a symptom of psoriasis, comprising identifying a patient suffering from or at risk of developing psoriasis, and orally administering to said patient a composition comprising *Bacillus coagulans* bacteria in an amount effective to reduce serum TNF-α levels in said patient.

Jovanka Lukic et al. in Wound Repair Regen. 2017 November, 25(6), p. 912-922 review the role of beneficial probiotic species in tissue repair. In particular, is reported that *Streptococcus salivarius*, commensal of oral epithelium, is a very potent inhibitor of *St. pyogenes*, a pathogen that causes pharyngitis and also cutaneous infections. However, nothing is said in this article about psoriasis or other autoimmune diseases.

Thorleifsdottir R H et al. in J. Immunol. 2012 May 15, 188(10), p. 5160-5, have found that exacerbation of chronic psoriasis can be associated with streptococcal throat infections and conclude that tonsillectomy may have a beneficial effect on chronic psoriasis, because the palatine tonsils generate effector T cells that recognize keratin determinants in the skin.

Di Pierro F et al. in Drug Healthc. Patient Saf. 2016 Nov. 21; 8, p. 77-81, found that the daily use of BLIS K12 was associated with a concurrent and persisting reduction in the occurrence of pharyngeal, recurrent, streptococcal disease. Moreover, the benefits to children may also extend to a reduction of nonstreptococcal diseases, including tracheitis, viral pharyngitis, rhinitis, flu, laryngitis, acute otitis media, and enteritis.

Other *Streptococcus salivarius* strains have been deposited at the Deutesche Sammlung von Mikroorganismen Und Zellkulturen (DSM) and at the American Type Culture Collection (ATCC), with the following deposit numbers: ATCC 7073, ATCC 25975, ATCC 27945, ATCC BAA-1024, DSM 13084, DSM 13085 and BLIS M18 (ATCC BAA 2593 or DSM 14685).

It is worth to report that the strains DSM 13084 (also known by the acronym "K12") has been deposited at the ATCC under the accession number ATCC BAA-1024, while the strain DSM 13085 is also known by the acronym "K30" and ATCC BAA 2593 (also known as BLIS M18") has been deposited as DSM 14685.

The bacterial strain *Streptococcus salivarius* BLIS K12 (ATCC BAA-1024) has received by the Food and Drug Administration US patent (FDA) the qualification of safe product for human administration as a food supplement (Generally Recognized As Safe—GRAS) with the number 591 (GRAS No. 591).

Despite the large number of useful products for the treatment of psoriasis, in the medical field the need to have available new compositions useful for the prevention or the treatment of this pathology is still very much felt.

DESCRIPTION OF THE INVENTION

It has now been surprisingly found that *Streptococcus salivarius* is a useful agent for the preparation of compositions suitable in the prevention or the treatment of psoriasis.

The term "composition", in accordance with the present invention, is meant to refer to: pharmaceutical compositions that are suitable for the preparation of medicines or drugs, nutraceutical compositions and dietetic compositions, that is, suitable for the preparation of food supplements, functional foods, foods for special medical purposes, medical devices, solid, semisolid or liquid foods, which can be administered to babies, children or adults, of any type and form, provided that they are suitable for the administration to human beings.

According to the present invention, the expressions "treatment" or "treating" are intended to refer to activities designed to treat, mitigate the symptoms, delay or stop the progression of a disease or a pathological condition.

The expressions "prevention" or "prevent" are intended to refer to activities aimed at minimizing the incidence or the effects of a disease or a pathological condition and/or at delaying or preventing the onset of a disease or a pathological condition.

It is therefore an object of the present invention *Streptococcus salivarius* for use in the prevention and/or the treatment of psoriasis, in which the type of psoriasis includes psoriasis vulgaris or plaque psoriasis, guttate or eruptive psoriasis, pustular psoriasis, erythrodermic psoriasis, inverse (or reversed) psoriasis and arthropathic psoriasis, and in which said *Streptococcus salivarius* is orally administered.

It is a further object of the present invention the *Streptococcus salivarius* for use in the prevention and/or the treatment of psoriasis, wherein the composition/unit dose to be administered (in the morning and/or in the evening) comprises an amount of *Streptococcus salivarius* from $0.1 \times 10^9$ to $10 \times 10^9$, preferably from $0.5 \times 10^9$ a $5 \times 10^9$, most preferably $1 \times 10^9$ CFU (Colony Forming Units) per dosage unit form (for example tablet, vial or sachet).

It is a further subject of the present invention *Streptococcus salivarius* for use in the prevention and/or the treatment of psoriasis, in which the composition/unit dose to be administered (in the morning and/or in the evening) comprises an amount of *Streptococcus salivarius* of $2 \times 10^9$ CFU per dosage unit form.

It is a further subject of the present invention the *Streptococcus salivarius* for use in the prevention and/or treatment of psoriasis, in which the composition/unit dose to be administered (in the morning and/or in the evening) comprises an amount of *Streptococcus salivarius* greater than $2 \times 10^9$ CFU per dosage unit form.

For "dosage unit" in accordance with the present invention it is intended a single tablet, sachet, vial, bar, snack and drink or analogues thereof, comprising *Streptococcus salivarius*.

It is a further object of the present invention an orally administrable composition, comprising as active ingredient or component *Streptococcus salivarius*, and optionally one or more pharmaceutically acceptable excipients and/or diluents, for use in the prevention and/or the treatment of psoriasis; the type of psoriasis includes psoriasis vulgaris or plaque psoriasis, guttate or eruptive psoriasis, pustular psoriasis, erythrodermic psoriasis, inverse (or reversed) psoriasis and psoriatic arthropathy.

It is a further object of the present invention a composition, which can be orally administered, comprising as active ingredient or component *Streptococcus salivarius* at a dose from $0.1 \times 10^9$ to $10 \times 10^9$, preferably from $0.5 \times 10^9$ to $5 \times 10^9$, very preferably $1 \times 10^9$ CFU, per dosage unit to be administered, and optionally one or more pharmaceutically acceptable excipients and/or diluents, for use in the prevention and/or the treatment of psoriasis.

It is a further object of the present invention an orally administrable composition, comprising as active ingredient or component *Streptococcus salivarius* at a dose of $2 \times 10^9$ CFU per unit dosage, and optionally one or more pharmaceutically acceptable excipients and/or diluents, for use in the prevention and/or the treatment of psoriasis.

It is a further object of the present invention an orally administrable composition, comprising as active ingredient or component *Streptococcus salivarius* at a dose greater than $2 \times 10^9$ CFU, per dose unit to be administered, and optionally one or more pharmaceutically acceptable excipients and/or diluents, for use in the prevention and/or the treatment of psoriasis.

It is a further object of the present invention an orally administrable composition, comprising as active ingredient or component *Streptococcus salivarius*, wherein said *Streptococcus salivarius* is added/dissolved in the dosage unit in the form of dry powder having a weight of 1 to 50 mg, preferably from 10 to 30 mg, most preferably 20 mg; and optionally one or more pharmaceutically acceptable excipients and/or diluents, for use in the prevention and/or the treatment of psoriasis; where in said dry powder the amount (in CFU) of *Streptococcus salivarius* above reported is present.

By "dry powder" according to the present invention it is meant, for example, the lyophilizate obtained from the bacterial culture provided by industrial production plant. It is evident that in the unitary composition (or dosage unit) the active agent can be present in any manner known to those skilled in the art and can be used for the preparation of a composition/unit dose.

It is a further object of the present invention an orally administrable pharmaceutical composition, comprising as active ingredient or component *Streptococcus salivarius*, wherein said *Streptococcus salivarius* is added/dissolved in the unit composition in the form of dry powder having a weight of less than 20 mg; and optionally one or more pharmaceutically acceptable excipients and/or diluents; for the use in the prevention and/or treatment of psoriasis; where in said dry powder the amount (in CFU) of *Streptococcus salivarius* above reported is present.

In accordance with the present invention, the orally administrable compositions comprising as active ingredient *Streptococcus salivarius* can be in liquid, solid or semisolid or dried powder, lyophilized or frozen; in a bottle, tablet or sachet; spray; or dissolved/dispersed in conventional food or beverage products, such as for example snacks, sweets, chocolate, yoghurt, cereals for breakfast, cheeses, chewing gums, desserts, whole or skimmed milk, fresh, preserved or frozen, or milk-based products or mixtures thereof, gelatins, puddings, fillings, corn, bread, paste, nuts or their derivatives/analogues; derived from the processing of the fruit, such as for example fruit juices, soft sweets, sauces, dressing or syrups.

According to a preferred embodiment of the invention, the composition is in the form of orosoluble tablets, more preferably fast-disintegrating or fast-dissolving tablets.

In accordance with the present invention, the route of administration by "nasal spray" is also provided. Suitable formulations for administration in the form of nasal spray are well known to a person skilled in the art.

The compositions according to the present invention may further contain antioxidants, vitamins, microelements, herbal extracts and/or further bacterial strains, for use in human.

As reported above, the bacterial strain *Streptococcus salivarius* BLIS K12 (ATCC BAA-1024) has received by the Food and Drug Administration US (FDA) the qualification of safe product for human administration as a food supplement (Generally recognized as safe) with the number "GRAS No. 591".

It is evident that, in accordance with the present invention, it is possible to use any strain of *Streptococcus salivarius*, which can be administered to humans.

Moreover, as regards the amount in CFU and the quantity in mg of dry powder containing *Streptococcus salivarius*, reference is made to or it is suggested to follow the teachings given in GRAS No. 591 at the link https://www.fda.gov/downloads/Food/IngredientsPackagingLabeling/CTRAS/NoticeInventory/UCM49455-pdf.

With the expression "functional food" is intended to include the foods characterized by additional effects due to the presence of components (generally not nutrients) naturally present or added, which interact more or less selectively with one or more physiologic functions of an organism (biomodulation) leading to positive effects on the maintenance of health and/or prevention of diseases. A food can be considered "functional", if its beneficial influence on one or more functions of the body is sufficiently demonstrated, in addition to suitable nutritional effects, to the extent of being relevant to a state of wellbeing and health or for the reduction of the risk of a disease. The beneficial effects could consist either in the maintenance or in the promotion of a state of well-being or health and/or in a reduction of the risk of a pathological process or of a disease (see Diplock A. T. et al: Scientific concepts of functional foods in Europe: Consensus document, British Journal of Nutrition 1999, 81 (suppl. 1), S1-S27).

It is a further object of the present invention a dietary supplement containing the composition of the present invention in one of the forms previously illustrated.

With the expression "dietary supplement" (DS) it is meant a food product intended to supplement the common diet and which forms a concentrated source of nutrients, such as vitamins and minerals or other substances having a nutritional or physiological effect in pre-dosed forms (see also Directive 2002/46/CE of Jun. 10 2002 and Italian Law Decree N. 169, Art. 2, of May 21, 2004).

It is also an object of the present invention a food for special medical purposes (FSMP) containing the composition of the present invention in one of the forms previously illustrated.

With the expression "food for special medical purposes" (FSMP) it is meant as defined in the US Regulation (NO 609/2013), as well as in the Guidelines issued by EFSA (European Food Safety Authority) entitled "Scientific and technical guidance on food for medical purposes especially in the context of Article 3 of Regulation (EU) No 609/2013"—EFSA Journal 2015; 13 (11):430. In particular, this regulatory definition is articulated into three points:

1) a food specially processed or formulated and intended for the dietary management of patients, including babies, to be used "under medical control" (medical supervision);
2) intended for exclusive or partial feeding of patients with limited, disturbed or altered capacity to assume, digest, absorb, metabolize or eliminate common foods or determined nutrients contained in them or metabolites, or with other nutritional requirements determined by clinical conditions;
3) whose dietary management cannot be carried out exclusively by modifying the normal diet. To be proposed and framed as FSMP, a product must meet the three points of the preceding definition.

For the purposes of distinction with the DS, it should be also pointed out that, while the latter products are conforming to the standard definition directive 2002/46/CE, even if they only perform "physiological" beneficial effects for the supply of the nutrients without any co-participation in the establishment of the food ration (for example vegetable extracts), the FSMP must necessarily have a "nutrient" role, as constituents of a food ration aimed at satisfying the nutritional requirement of patients in specific nutritional vulnerability conditions.

It is also an object of the present invention a medical device containing the composition of the present invention in one of the forms previously illustrated.

With the expression "medical device" it is intended a product, used alone or in combination, intended by the manufacturer to be used in humans for purposes of:

diagnosis, prevention, control, therapy or attenuation of a disease;

diagnosis, control, therapy, attenuation or compensation for an injury or a handicap;

study, replacement or modification of the anatomy or a physiological process;

whose main desired action in or on the human body is not achieved with pharmacological or immunological means or by metabolism, but whose function can be assisted by these means (see Directive 93/42/EEC of 42 Jun. 14 1993 concerning the medical devices and subsequent amendments thereto).

As far as excipients and/or diluents to be placed on the market that may be used in the compositions according to the invention, reference is made to what has been widely reported in the literature and well known to the experts in pharmaceutical technology.

The excipients are grouped according to various classifications, depending on the functional role that are designed to perform in the resulting formulation. For example, in solid dosage forms, one can add the following classes of excipients: diluents, for example lactose, microcrystalline cellulose; disintegrants, for example sodium starch glycolate, sodium croscarmellose; binders, for example PVP, HPMC; lubricants, for example magnesium stearate; glidants, for example colloidal $SiO_2$.

The following examples illustrate the invention without limiting it and refer to the following Figures.

DESCRIPTION OF THE FIGURES

FIG. 1 shows the clinical images of a patient at time 0 and after 4 weeks from the beginning of the therapy with the probiotic of the invention. For the same patient and at the given times the values of PASI (Psoriasis area and Severity Score) are also shown.

EXAMPLES

Example 1

Clinical Study 1

Figure 1:
FIG. 1.
Figure 1:
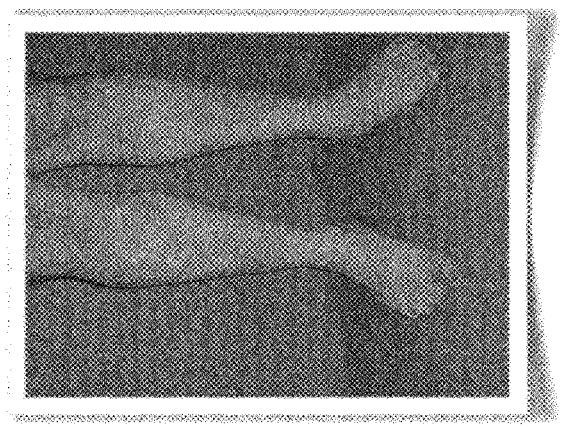
Figure 1:
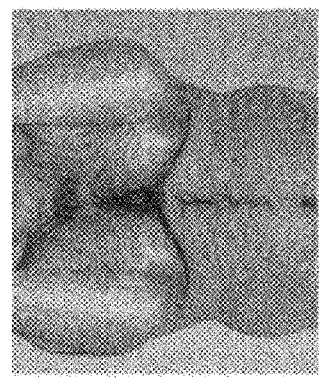
Figure 1:
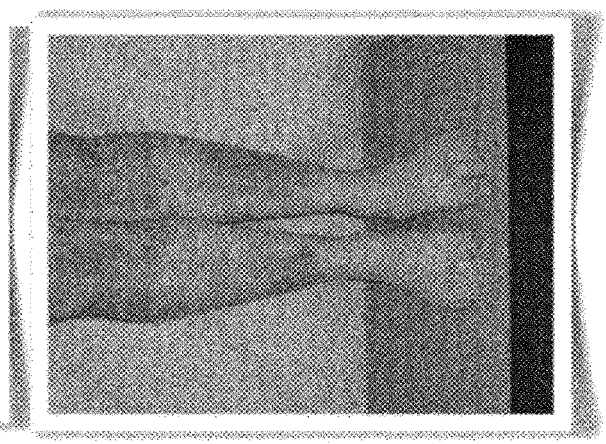

A clinical study was carried out useful for the evaluation of the therapeutic efficacy of *Streptococcus salivarius* in patients affected by psoriasis vulgaris, guttate and arthropathic psoriasis.

The strain of *Streptococcus salivarius* used was the K12 (BLIS® K12); in the form of slow-melt buccal discoids, 1,000 mg orosoluble tablets containing granular powder, 1 billion CFU, provided with the due authorisations for use in human (hereinafter also called "probiotic").

However, according to the present invention, different food supplements containing different strains of *Streptococcus salivarius* could have been used, provided that they have the necessary the authorizations for human administration.

To 20 patients, the evening before sleeping and after tooth brushing, a BLIS® K12 tablet was administered to be slowly dissolved in the mouth. The patients had the following characteristics: aged between 14 and 70 years, of both sexes, suffering from mild to moderate psoriasis vulgaris or guttate psoriasis and not associated with other cutaneous and/or systemic diseases.

To 20 patients, the evening before sleeping and after tooth brushing, a tablet of BLIS® K12 was administered to be slowly dissolved in the mouth. The patients had the following characteristics: between the ages of 40 and 70, of both sexes, suffering from moderate to severe arthropathic psoriasis.

A further group, a control group consisting of 20 healthy individuals, was enrolled in the clinical study and such group of individuals received the same administration of the two previous groups.

At the beginning of the study all patients were subjected to dermatological and laboratory clinical examination, such as VES, PCR, urine analysis was carried out and, in the case of patients with the arthropathic form, an articular echography was also carried out. Within the scope of dermatological evaluation the parameter, "Psoriasis area and disease Severity Score (PASI)", was also evaluated, and, in psoriatic patients, the average starting value of this parameter was 8.

After 4 weeks of treatment, the PASI and the clinical, echography and laboratory evaluations were repeated.

From the first experimental results obtained, it was found that 80% of the treated patients showed complete remission of the cutaneous pathology, while in patients with an arthropathic form, a stabilization of the joint pathology was documented.

After 12 weeks of treatment, the PASI and the clinical and laboratory evaluations were further repeated and, from this evaluation, it became clear that all the patients achieved complete remission. The considered disease parameter (PASI) showed a considerable reduction in the course of the therapy, with a zeroing of the same at the end of the treatment. At the end of the therapy, the chemical tests with the inflammatory indexes were within the normal values.

In patients affected by the arthropathic form, the stabilization of the articular pathology was documented through echography and an improvement in the articular symptom was reported. No patient treated, including the control group, reported the onset of side effects.

FIG. 1 shows the clinical images of one patient at time 0 and after 4 weeks from the beginning of therapy with the probiotic invention.

Figure 2:
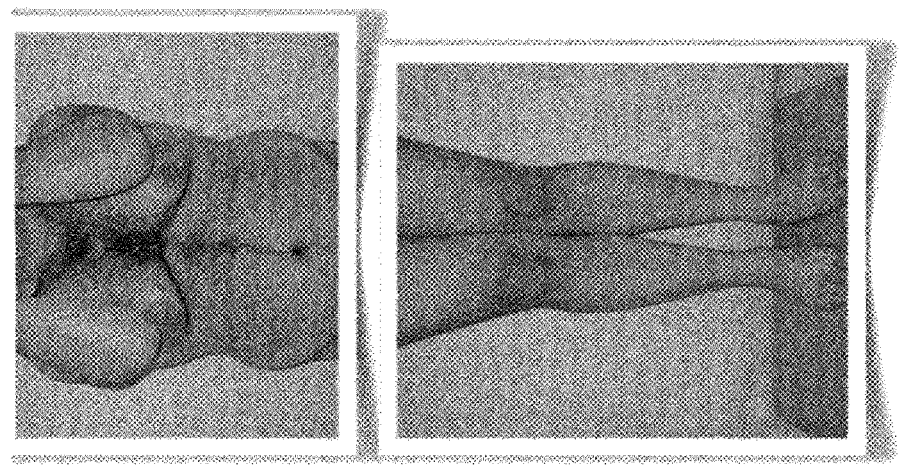
FIG. 2 shows the clinical images of a patient after 8 and 12 weeks from the beginning of the therapy with the probiotic invention. For the same patient and at the given times the values of PASI are also shown.
Figure 2:
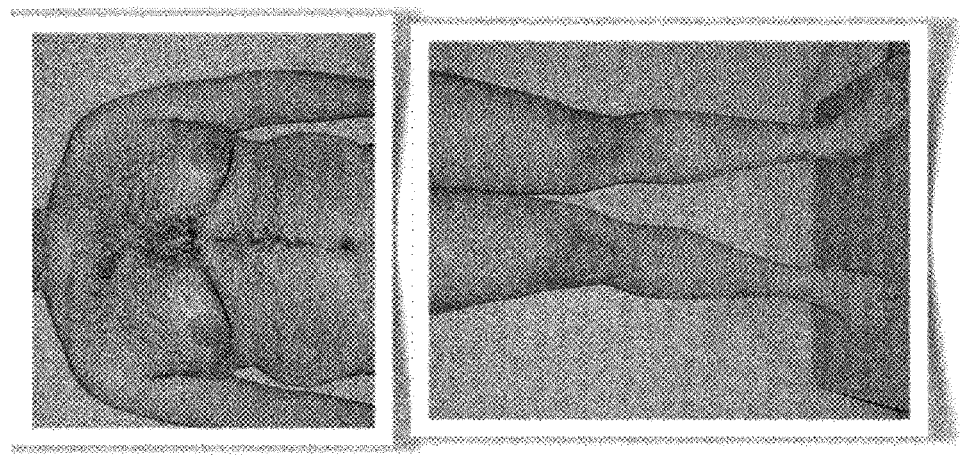

FIG. 2 shows the clinical images of one patient after 8 and 12 weeks from the beginning of the therapy with the probiotic invention.

Example 2

Clinical Study 2

As second clinical trial was carried out as described in Example 1. In total, 29 psoriasis patients were enrolled, 17 men and 12 women.

The patients were divided into three different groups based on the treatment administered to them.

The first group was treated with ToothGuard™ lozenges, one lozenge per day, (each lozenge containing at least 2.50 billion CFU/dose at the date of manufacture of *Streptococcus salivarius* BLIS M18, kindly provided by BLIS Technologies Ltd.) in accordance with the invention; the second group was treated with BIOTEBACT® (a food supplement containing a tindalized strain of *Lactobacillus helveticus* MIMLh5, sold by Inpha Nutriceuticals 2000), 2 tablets of 400 mg per day (each tablet of 400 mg containing 1 billion non-viable cells of *Lactobacillus helveticus*, 30 mg of erysmo extract, and 40 mg of sodium hyaluronate from which 38 mg of hyaluronic acid), for comparative purposes; and the third group was treated with Benoit *Bifidobacterium*™ capsules (a food supplement of probiotic microorganisms containing a mixture of live *Bifidobacterium longum, Bifidobacterium breve* and *Bifidobacterium bifidum*, sold by Alchimia Benoit®), 2 capsules per day (each capsule containing *Bifidobacterium longum* 100 MLD CFU/g; *Bifidobacterium breve* 100 MLD CFU/g; *Bifidobacterium bifidum* 100 MLD CFU/g, inositol, fructoligosaccarides (FOS) and inulin), for comparative purposes. The treatment lasted 4 weeks for the all the groups of patients.

The mean age of the patients was 31.71 years, while most of the patients were in age group of 21-30 years. The mean duration of the disease was 7.54 years. All patients were suffering from the mild form of the disease (psoriasis vulgaris or plaque psoriasis and guttate form).

The results of the study for the three groups of patients at the end of the 4 weeks of treatment is reported in the following Table 1, Comparative Table 1 and Comparative Table 2.

TABLE 1

(treatment with *Streptococcus salivarius*)

| Patient number | Type of Psoriasis | Patient Age | PASI T0 | PASI T4 | Adverse Events |
|---|---|---|---|---|---|
| 1 | plaque | 32 | 4 | 0 | 0 |
| 2 | plaque | 41 | 8 | 0 | 0 |
| 3 | guttate | 23 | 0.8 | 0 | 0 |
| 4 | plaque | 15 | 2 | 0 | 0 |
| 5 | plaque | 45 | 6 | 4 | 0 |
| 6 | plaque | 25 | 3 | 0 | 0 |
| 7 | guttate | 18 | 0.8 | 0 | 0 |
| 8 | plaque | 31 | 2 | 0 | 0 |
| 9 | guttate | 19 | 6.2 | 2 | 0 |

COMPARATIVE TABLE 1

(treatment with *Lactobacillus helveticus*)

| Patient number | Type of Psoriasis | Patient Age | PASI T0 | PASI T4 | Adverse Events |
|---|---|---|---|---|---|
| 1 | plaque | 45 | 5 | 4 | 0 |
| 2 | guttate | 19 | 8 | 6.2 | 0 |
| 3 | guttate | 50 | 8 | 6.8 | 0 |
| 4 | plaque | 25 | 2 | 1.4 | 0 |
| 5 | plaque | 21 | 6 | 2 | 0 |
| 6 | plaque | 32 | 3 | 3 | 0 |
| 7 | plaque | 16 | 4 | 2 | 0 |
| 8 | plaque | 23 | 6 | 0 | 0 |
| 9 | plaque | 33 | 0.8 | 0 | 0 |
| 10 | guttate | 39 | 4 | 2 | 0 |

COMPARATIVE TABLE 2

(treatment with a mixture of *Bifidobacterium longum*, *B breve* and *B. bifidum*)

| Patient number | Type of Psoriasis | Patient Age | PASI T0 | PASI T4 | Adverse Events |
|---|---|---|---|---|---|
| 1 | guttate | 24 | 4 | 2 | 0 |
| 2 | plaque | 19 | 5 | 4 | 0 |
| 3 | guttate | 27 | 3 | 3 | 0 |
| 4 | plaque | 20 | 8 | 6.2 | 0 |
| 5 | plaque | 43 | 6 | 2 | 0 |
| 6 | plaque | 50 | 4 | 2 | 0 |
| 7 | plaque | 23 | 0.8 | 0 | 0 |
| 8 | plaque | 16 | 5 | 0 | 0 |
| 9 | guttate | 33 | 3 | 3 | 0 |
| 10 | plaque | 42 | 5 | 4.8 | 0 |

From the above-reported results, it is clear that the treatment with *Streptococcus salivarius* provided the best results in terms of PASI score improvement in most of the treated patients. All the patients treated with *Streptococcus salivarius* showed an improvement of the PASI score and the majority of them obtained a complete healing of the psoriatic skin lesions.

Example 3—Compositions

Compositions comprising *Streptococcus salivarius* are known in the art, have been on the market for a long time now and are of a quality suitable for human administration.

Though the daily dose will depend, according to the judgment of the practitioner, the subject's weight, age and general conditions, it is generally advisable to administer the *Streptococcus salivarius* orally once or twice a day.

Examples of compositions comprising *Streptococcus salivarius* are reported in the following Table 2.

TABLE 2

*Streptococcus salivarius*

| | Strain | Deposit No. | CFU |
|---|---|---|---|
| COMPOSITION 1 | K12 | ATCC BAA-1 024 | $1 \times 10^9$ |
| COMPOSITION 2 | K12 | ATCC BAA-1 024 | $2 \times 10^9$ |
| COMPOSITION 3 | K12 | ATCC BAA-1 024 | $>2 \times 10^9$ |
| COMPOSITION 4 | K30 | DSM 13085 | $1 \times 10^9$ |
| COMPOSITION 5 | K30 | DSM 13085 | $2 \times 10^9$ |
| COMPOSITION 6 | K30 | DSM 13085 | $>2 \times 10^9$ |
| COMPOSITION 7 | — | ATCC 7073 | $1 \times 10^9$ |
| COMPOSITION 8 | — | ATCC 7073 | $2 \times 10^9$ |
| COMPOSITION 9 | — | ATCC 7073 | $>2 \times 10^9$ |
| COMPOSITION 10 | — | ATCC 25975 | $1 \times 10^9$ |
| COMPOSITION 11 | — | ATCC 25975 | $2 \times 10^9$ |
| COMPOSITION 12 | — | ATCC 25975 | $>2 \times 10^9$ |
| COMPOSITION 13 | — | ATCC 27945 | $1 \times 10^9$ |
| COMPOSITION 14 | — | ATCC 27945 | $2 \times 10^9$ |
| COMPOSITION 15 | — | ATCC 27945 | $>2 \times 10^9$ |
| COMPOSITION 16 | 24SMBc | — | $1 \times 10^9$ |
| COMPOSITION 17 | 24SMBc | — | $2 \times 10^9$ |
| COMPOSITION 18 | 24SMBc | — | $>2 \times 10^9$ |
| COMPOSITION 19 | — | — | $1 \times 10^9$ |
| COMPOSITION 20 | — | — | $2 \times 10^9$ |
| COMPOSITION 21 | — | — | $>2 \times 10^9$ |
| COMPOSITION 22 | M18 | ATCC BAA 2593 | $1 \times 10^9$ |
| COMPOSITION 23 | M18 | ATCC BAA 2593 | $2 \times 10^9$ |
| COMPOSITION 24 | M18 | ATCC BAA 2593 | $>2 \times 10^9$ |

Non limiting examples of excipients are the following: fructose, trehalose, maltodextrin, silicon dioxide and/or aromas

The invention claimed is:

1. A method of treating psoriasis in patients in need thereof, said method comprising orally administering a pharmaceutically effective amount of a composition comprising *Streptococcus salivarius* to said patients.

2. The method according to claim 1, wherein the psoriasis is selected from the group consisting of psoriasis vulgaris, guttate psoriasis, pustular psoriasis, erythrodermic psoriasis, inverse or reversed psoriasis and psoriatic arthritis.

3. The method according to claim 1 wherein the daily dose of *Streptococcus salivarius* that is administered is from $0.1 \times 10^9$ to $10 \times 10^9$ CFU.

4. The method according to claim 1, wherein the daily dose of *Streptococcus salivarius* that is administered is selected from the group consisting of $1 \times 10^9$ CFU, $2 \times 10^9$ CFU and higher than $2 \times 10^9$ CFU.

5. A method of treating psoriasis in patients in need thereof, said method comprising administering orally to said patients a pharmaceutically effective amount of a composition comprising as an active principle component or ingredient *Streptococcus salivarius*, in one or more pharmaceutically acceptable excipients.

6. The method according to claim 5, wherein said composition is in solid, semisolid or liquid form.

7. The method according to claim 5, wherein said composition is in the form of a vial, a tablet, a sachet or a spray.

8. The method according to claim 5, wherein said composition is in the form of a food or a drink selected from the group consisting of: snacks, sweets, chocolate, yogurt, cereals, cheeses, chewing gums, desserts, fresh, preserved or frozen whole milk, skimmed milk, milk-based products or mixtures thereof, jellies, puddings, cereals, bread, pasta, nuts and fruit-derived products, wherein the fruit-derived products are selected from the group consisting of fruit juices, soft candies, sauces, condiments and syrups.

9. The method according to claim 5, wherein said composition further comprises antioxidants, vitamins, micronutrients, plant extracts and/or further bacterial strains.

10. The method according to claim 3, wherein the daily dose of *Streptococcus salivarius* that is administered is from $0.5 \times 10^9$ to $5 \times 10^9$ CFU.

11. The method according to claim 3, wherein the daily dose of *Streptococcus salivarius* that is administered is $1 \times 10^9$ CFU.

* * * * *